United States Patent [19]

Onodera et al.

[11] Patent Number: 5,932,753

[45] Date of Patent: Aug. 3, 1999

[54] PROCESS FOR PRODUCING 2-METHYL-1,4-BENZOQUINONE

[75] Inventors: Kenji Onodera, Ohmiya; Eiko Nakatu, Utsunomiya; Masayuki Kobayashi, Kawaguchi, all of Japan

[73] Assignee: Chuo Chemical Co., Inc., Tokyo, Japan

[21] Appl. No.: 09/020,827

[22] Filed: Feb. 9, 1998

[30] Foreign Application Priority Data

Feb. 19, 1997 [JP] Japan .................................... 9-050985

[51] Int. Cl.$^6$ .................................................... C07C 50/04
[52] U.S. Cl. ........................... 552/309; 552/293; 552/303; 568/338; 568/357; 568/362
[58] Field of Search ..................................... 552/293, 303, 552/309; 568/338, 357, 361, 362; 502/225

[56] References Cited

U.S. PATENT DOCUMENTS

| 3,210,384 | 10/1965 | Hay | 260/396 |
| 4,257,968 | 3/1981 | Reilly | 260/396.2 |

FOREIGN PATENT DOCUMENTS

| 60-51144 | 3/1985 | Japan . |
| 62-148446 | 7/1987 | Japan . |
| 63-17842 | 1/1988 | Japan . |
| 63-41438 | 2/1988 | Japan . |
| 6-57669 | 8/1994 | Japan . |
| 7-42244 | 5/1995 | Japan . |
| 07-223992 | 8/1995 | Japan . |
| 7-76192 | 8/1995 | Japan . |

OTHER PUBLICATIONS

Database WPI, Section CH, Week 8813, Derwent Publications Ltd., London, GB, Class E14, AN 88–089187 of JP 63 041 438 A, Feb. 22, 1988.

Database WPI, Section CH, Week 8532, Derwent Publications Ltd., London, GB, Class B05, AN 85–194645, Jul. 2, 1985.

*Primary Examiner*—Shailendra Kumar
*Assistant Examiner*—Sreeni Padmanabhan
*Attorney, Agent, or Firm*—Frishauf, Holtz, Goodman, Langer & Chick, P.C.

[57] ABSTRACT

A process for producing 2-methyl-1,4-benzoquinone at a high conversion, a high selectivity and at a low cost by oxidizing m-cresol with oxygen at a low partial pressure in the presence of at least one copper (I) halide catalyst and a mixed solvent of ketone and acetonitrile. The 2-methyl-1,4-benzoquinone is useful as an intermediate compound to produce vitamin K.

18 Claims, No Drawings

PROCESS FOR PRODUCING 2-METHYL-1,4-BENZOQUINONE

BACKGROUND OF THE INVENTION

1. Field of the Invention

The present invention relates to an improved process for producing 2-methyl-1,4-benzoquinone. More particularly, the present invention relates to a process for industrially advantageously producing 2-methyl-1,4-benzoquinone useful as an intermediate compound for producing Vitamin K by oxidizing m-cresol with molecular oxygen with a high conversion and a high selectivity at a low cost for facilities for the production.

2. Description of the Related Arts

Vitamin K is known as an antihemorrhagic vitamin and includes various types, such as vitamin $K_1$ (phytonadione), vitamin $K_2$ (menatetorenone), vitamin $K_3$ (menadione), and vitamin $K_3$ sodium hydrogensulfite (menadione sodium hydrogensulfite). Among these vitamins, menadione sodium hydrogensulfite is used in a large amount as an additive to feed.

These types of Vitamin K are prepared by using 2-methyl-1,4-naphthoquinone as the starting material (vitamin $K_3$ is 2-methyl-1,4-naphthoquinone itself). 2-Methyl-1,4-naphthoquinone has heretofore been industrially produced by oxidation of 2-methylnaphthalene with chromic anhydride. However, this process has a problem in that 6-methyl-1,4-naphthoquinone which is an isomer of 2-methyl-1,4-naphthoquinone is formed at the same time, and efficient separation of 6-methyl-1,4-naphthoquinone is difficult. Therefore, the yield is as low as 20 to 50%.

As the process for producing 2-methyl-1,4-naphthoquinone with a high yield, a process for producing 2-methyl-1,4-naphthoquinone by oxidation of a product of Diels Alder reaction of 2-methyl-1,4-benzoquinone and 1,3-butadiene was recently proposed (Japanese Patent Application Laid-Open No. Heisei 7(1995)-223992). Therefore, 2-methyl-1,4-naphthoquinone can be a very useful intermediate compound for producing vitamin K when 2-methyl-1,4-benzoquinone can be obtained at a low cost.

As the process for producing 2-methyl-1,4-benzoquinone, for example, a process in which o-toluidine is oxidized with manganese dioxide in a dilute sulfuric acid and a process in which m-cresol is oxidized with molecular oxygen are known. When these two process are compared, the process in which m-cresol is oxidized with molecular oxygen is industrially more advantageous because, in the process comprising oxidizing o-toluidine, expensive manganese dioxide must be used and also waste disposal causes problems.

As the process in which m-cresol is oxidized with molecular oxygen, various processes have been proposed. Examples of such processes include (1) a process in which an alkylphenol is brought into reaction with oxygen in a methanol solvent in the presence of a catalyst comprising a copper(II) halide and hydroxide of an alkali metal or alkaline earth metal and an accelerator comprising a halide of an alkali metal or an alkaline earth metal (Japanese Patent Application Laid-Open No. Showa 60(1985)-51144); (2) a process in which a phenol is brought into reaction with oxygen in an alcohol solvent in the presence of copper(II) chloride and an alkali metal chloride (Japanese Patent Publication No. Heisei 6(1994)-57669); (3) a process in which a phenol is brought into reaction with oxygen in a methanol solvent in the presence of copper(I) chloride and an alkali metal chloride (Japanese Patent Publication No. Heisei 7(1995)-42244); and (4) a process in which a phenol is brought into reaction with oxygen in a methanol solvent in the presence of copper(II) chloride and an alkali metal chloride (Japanese Patent Publication No. Heisei 7(1995)-76192).

However, process (1) is not always satisfactory because the conversion is small in the oxidation of m-cresol although the reaction condition is relatively mild. Processes (2) to (4) have drawbacks in that these processes require a high pressure of oxygen (for example, the preferable pressure of oxygen in process (2) is 20 to 150 $kg/cm^2$, the required pressure in process (3) is 30 $kg/cm^2$ or higher, and the preferable pressure in process (4) is 30 $kg/cm^2$ or higher), which inevitably causes a higher cost of facilities for the production, and that no example can be found about using m-cresol as the phenol.

SUMMARY OF THE INVENTION

Accordingly, the present invention has an object of solving the problems of conventional processes for producing 2-methyl-1,4-benzoquinone and providing a process for industrially advantageously producing 2-methyl-1,4-benzoquinone by oxidation of m-cresol with molecular oxygen with a high conversion and a high selectivity at a low cost for facilities for the production.

As the result of extensive studies by the present inventors to achieve the above object, it was found that 2-methyl-1,4-benzoquinone can efficiently be obtained at a low partial pressure of oxygen with a high conversion and a high selectivity when m-cresol is oxidized with molecular oxygen in the presence of a specific catalyst, and thus the object can be achieved. The present invention has been completed on the basis of this knowledge.

Accordingly, the present invention provides:

(1) A process for producing 2-methyl-1,4-benzoquinone comprising oxidizing m-cresol with molecular oxygen in the presence of a copper(I) halide catalyst in a mixed solvent containing a ketone and acetonitrile;

(2) A process described in (1), wherein the mixed solvent contains the ketone in an amount of 10 to 90% by weight;

(3) A process described in any of (1) and (2), wherein the ratio by weight of the mixed solvent to m-cresol is 1 to 30;

(4) A process described in any of (1) to (3), wherein the ketone is acetone.;

(5) A process described in any of (1) to (4), wherein the copper(I) halide is used in amount of 0.01 to 2.0 mol per 1 mol of m-cresol;

(6) A process described in any of (1) to (5), wherein the oxidation reaction is conducted at a partial pressure of oxygen of 1 to 20 $kg/cm^2$; and (7) A process described in any of (1) to (6), wherein the oxidation reaction is conducted at a reaction temperature of 0 to 50° C.

DESCRIPTION OF THE PREFERRED EMBODIMENTS

In the process of the present invention, a mixed solvent containing a ketone and acetonitrile is used as the solvent. The type of the ketone is not particularly limited, and various ketones can be used. Examples of the ketone include aliphatic ketones, such as acetone, methyl ethyl ketone, and methyl isobutyl ketone, and alicyclic ketones, such as cyclopentanone and cyclohexanone. Among these ketones, acetone is preferable from the standpoint of the reactivity and the yield. The ketone may be used singly or as a combination of two or more types. The content of the ketone in the mixed solvent is preferably in the range of 10 to 90% by weight. When the content is less than 10% by weight, the selectivity is occasionally decreased because portions of the raw materials and reaction products form resins. When the content exceeds 90% by weight, there is the tendency that the conversion is decreased. The preferable content of the ketone in the mixed solvent is in the range of 50 to 70% by weight from the standpoint of the balance between the selectivity and the conversion. Water in such an amount as that formed by the reaction does not affect the reaction. Other organic solvents may be added to the mixed solvent in a suitable amount, where desired, as long as the object of the present invention is not adversely affected.

In the process of the present invention, it is necessary that a copper(I) halide be used as the catalyst. The type of the copper(I) halide is not particularly limited. Examples of the copper(I) halide include copper(I) chloride, copper(I) bromide, and copper(I) iodide. The copper(I) halide may be used singly or as a combination of two or more types. Copper(I) chloride is preferably used from the standpoint of the effect. The amount used of the copper(I) halide is not particularly limited. From the standpoint of the effect, an amount in the range of 0.01 to 2.0 mol per 1 mol of m-cresol is preferable, and an amount in the range of 0.05 to 1.0 mol per 1 mol of m-cresol is more preferable.

In the process of the present invention, where desired, a halide or a hydroxide of an alkali metal or an alkaline earth metal may suitably be used as the reaction accelerator in combination with the above catalyst as long as the object of the present invention is not adversely affected. Examples of the halide of an alkali metal or an alkaline earth metal include sodium chloride, potassium chloride, magnesium chloride, and calcium chloride. Examples of the hydroxide of an alkali metal or an alkaline earth metal include sodium hydroxide, potassium hydroxide, lithium hydroxide, calcium hydroxide, and magnesium hydroxide.

In the process of the present invention, the relative amounts of the mixed solvent and m-cresol are not particularly limited. It is advantageous that the ratio by weight of the mixed solvent to m-cresol is selected in the range of 1 to 30. When the ratio is less than 1, the selectivity tends to be decreased. When the ratio exceeds 30, the volume efficiency of the reactor is inferior. The preferable ratio by weight of the mixed solvent to m-cresol is in the range of 5 to 20 from the standpoint of the selectivity and the volume efficiency.

In the process of the present invention, m-cresol is oxidized with molecular oxygen. As the molecular oxygen, oxygen gas, air, or a mixture of oxygen with various types of inert gas, such as nitrogen, argon, and helium, can be used.

In the oxidation reaction in accordance with the process of the present invention, the partial pressure of oxygen is not particularly limited and is generally selected in the range of 1 to 20 $kg/cm^2$. When the partial pressure of oxygen is less than 1 $kg/cm^2$, there is the possibility that the reaction is slow and the selectivity is decreased. When the partial pressure of oxygen exceeds 20 $kg/cm^2$, the cost of facilities for the production is increased. Therefore, such partial pressures are not preferable. The preferable partial pressure of oxygen is in the range of 3 to 15 $kg/cm^2$ from the standpoint of the reaction rate, the selectivity, and the cost of facilities for the production.

As for the reaction temperature, an excessively low temperature is not practical because of an excessively low reaction rate, and an excessively high temperature causes decrease in the selectivity. From the standpoint of the balance between the reaction rate and the selectivity, the reaction temperature is preferably in the range of 0 to 50° C., more preferably in the range of 10 to 30° C. The reaction time depends on the reaction temperature, the partial pressure of oxygen, and other conditions and cannot be generally defined. The reaction time is generally in the range of 1 to 24 hours, preferably in the range of 3 to 15 hours. The oxidation reaction may be conducted in accordance with any of batch processes and continuous processes.

As for the method of addition of m-cresol into the mixed solvent when the reaction is conducted, m-cresol may be added dropwise into the mixed solvent. The control of the reaction temperature is facilitated by using this method.

The method of separation of 2-methyl-1,4-benzoquinone from the fluid obtained after the reaction has been completed is not particularly limited. After the fluid is filtered to remove the catalyst, 2-methyl-1,4-benzoquinone can be obtained by a suitable method, such as distillation or steam distillation of the filtrate or crystallization from the filtrate.

To summarize the advantages of the present invention, in accordance with the process of the present invention, 2-methyl-1,4-benzoquinone is produced industrially advantageously by oxidizing m-cresol with molecular oxygen under a low partial pressure of oxygen with a high conversion and a high selectivity at a low cost of facilities for the production.

2-Methyl-1,4-benzoquinone obtained by the process of the present invention is useful as an intermediate compound for producing Vitamin K, and methylhydroquinone obtained by reduction of 2-methyl-1,4-benzoquinone is useful as an intermediate compound for synthesis of organic compounds.

EXAMPLES

The present invention is described more specifically with reference to the examples. However, the present invention is not limited by the examples.

Example 1

Into a glass autoclave having an inner volume of 1 liter, 100 g of acetone, 100 g of acetonitrile, 10.0 g of m-cresol (0.09 mol), and 1.85 g (ratio by mol to m-cresol: 0.2) of copper(I) chloride were placed. Then, oxygen was introduced into the autoclave until the pressure of oxygen reached 7 $kg/cm^2G$, and the autoclave was kept at 25° C. for 7 hours. Subsequently, the pressure in the autoclave was released. The content of the autoclave was taken out and analyzed by the high performance liquid chromatography to obtain the conversion of m-cresol, the selectivity to 2-methyl-1,4-benzoquinone, and the yield. The results are shown in Table 1.

Examples 2 to 5 and Comparative Examples 1 and 2.

m-Cresol was oxidized in accordance with the same procedures as those conducted in Example 1 under the conditions shown in Table 1 using various types of solvent and various relative amounts of the components of the mixed solvent. The results are shown in Table 1.

TABLE 1-1

| | solvent | | m-cresol (g) | catalyst[1] (ratio by mol) | temperature °C |
|---|---|---|---|---|---|
| | type | amount (g) | | | |
| Example 1 | CH₃CN<br>acetone | 100<br>100 | 10.0 | 0.2 | 25 |
| Example 2 | CH₃CN<br>acetone | 160<br>40 | 10.0 | 0.2 | 25 |
| Example 3 | CH₃CN<br>acetone | 60<br>140 | 10.0 | 0.2 | 25 |
| Example 4 | CH₃CN<br>acetone | 60<br>140 | 10.0 | 1.0 | 25 |
| Example 5 | CH₃CN<br>MEK[2] | 60<br>140 | 10.0 | 1.0 | 25 |
| Comparative Example 1 | CH₃CN | 200 | 10.0 | 0.2 | 25 |
| Comparative Example 2 | acetone | 200 | 10.0 | 0.2 | 25 |

TABLE 1-2

| | pressure of oxygen (kg/cm²G) | time (hr) | conversion (%) | selectivity (%) | yield (%) |
|---|---|---|---|---|---|
| Example 1 | 7 | 7 | 99.5 | 93.2 | 92.7 |
| Example 2 | 7 | 7 | 99.8 | 85.3 | 85.1 |
| Example 3 | 7 | 7 | 91.7 | 94.0 | 86.2 |
| Example 4 | 7 | 7 | 100 | 88.0 | 88.0 |
| Example 5 | 7 | 7 | 99.6 | 89.6 | 89.2 |
| Comparative Example 1 | 7 | 7 | 100 | 77.8 | 77.8 |
| Comparative Example 2 | 7 | 7 | 2.2 | trace | trace |

[1]Catalyst (ratio by mol): ratio by mol of copper(I) chloride to m-cresol
[2]MEK: methyl ethyl ketone

What is claimed is:

1. A process for producing 2-methyl-1,4-benzoquinone comprising oxidizing m-cresol with molecular oxygen in the presence of at least one copper(I) halide catalyst in a mixed solvent containing a ketone and acetonitrile.

2. A process according to claim 1, wherein the mixed solvent contains the ketone in an amount of 10 to 90% by weight.

3. A process according to claim 1, wherein the ratio by weight of a mixed solvent to the m-cresol is 1 to 30.

4. A process according to claim 1, wherein the ketone is acetone.

5. A process according to claim 1, wherein the copper(I) halide is in an amount of 0.01 to 2.0 mol per 1 mol of the m-cresol.

6. A process according to claim 1, wherein the oxidizing is conducted at a partial pressure of oxygen of 1 to 20 kg/cm².

7. A process according to claim 1, wherein the oxidizing is conducted at a reaction temperature of 0 to 50° C.

8. A process according to claim 2, wherein the ketone is selected from the group consisting of acetone, methyl ethyl ketone, methyl isobutyl ketone, cyclopentanone and cyclohexanone.

9. A process according to claim 8, wherein the mixed solvent contains the ketone in an amount of 50 to 70% by weight.

10. A process according to claim 9, wherein the at least one copper (I) halide catalyst is selected from the group consisting of copper (I) chloride, copper (I) bromide and copper (I) iodide.

11. A process according to claim 10, wherein the at least one copper (I) halide is in an amount of 0.05 to 1 mol per 1 mol of the m-cresol.

12. A process according to claim 11, wherein a ratio by weight of the mixed solvent to the m-cresol is 5 to 20.

13. A process according to claim 12, wherein the oxidizing is carried out at a pressure of 3 to 15 kg/cm², at a temperature of 10 to 30° C. and for a reaction time of 7 to 24 hours.

14. A process according to claim 13, wherein the reaction time is 3 to 15 hours.

15. A process according to claim 14, wherein the ketone is acetone.

16. A process according to claim 15, wherein the at least one copper (I) halide is copper (I) chloride.

17. A process according to claim 16, which further comprises the process being carried out in the presence of a reaction accelerator selected from the group consisting of sodium chloride, potassium chloride, magnesium chloride, calcium chloride, sodium hydroxide, potassium hydroxide, lithium hydroxide, calcium hydroxide and magnesium hydroxide.

18. A process according to claim 16, wherein the pressure is 7 kg/cm²G.

* * * * *